# (12) United States Patent
Takeuchi et al.

(10) Patent No.: US 9,060,903 B2
(45) Date of Patent: Jun. 23, 2015

(54) PANTS-TYPE DISPOSABLE WEARING ARTICLE

(75) Inventors: Mariko Takeuchi, Kanonji (JP);
Toshifumi Otsubo, Kanonji (JP);
Tatsuya Hashimoto, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 427 days.

(21) Appl. No.: 13/515,411

(22) PCT Filed: Dec. 27, 2010

(86) PCT No.: PCT/JP2010/007573
§ 371 (c)(1),
(2), (4) Date: Jun. 12, 2012

(87) PCT Pub. No.: WO2011/080919
PCT Pub. Date: Jul. 7, 2011

(65) Prior Publication Data
US 2012/0253307 A1 Oct. 4, 2012

(30) Foreign Application Priority Data
Dec. 28, 2009 (JP) .................................. 2009-298963

(51) Int. Cl.
*A61F 13/15* (2006.01)
*A61F 13/496* (2006.01)

(52) U.S. Cl.
CPC .................................. *A61F 13/4963* (2013.01)

(58) Field of Classification Search
USPC .................. 604/396, 385.22, 385.24, 385.27, 604/385.29, 385.3, 385.26
See application file for complete search history.

(56) References Cited

U.S. PATENT DOCUMENTS 4,209,563 A * 6/1980 Sisson .......................... 442/329
4,909,804 A 3/1990 Douglas, Sr.
(Continued)

FOREIGN PATENT DOCUMENTS

| EP | 923920 | 6/1999 |
| JP | 61207605 | 9/1986 |

(Continued)

OTHER PUBLICATIONS

International Search Report for PCT/JP2010/007573 mailed Mar. 15, 2011.
(Continued)

*Primary Examiner* — Jacqueline Stephens
(74) *Attorney, Agent, or Firm* — Lowe Hauptman & Ham, LLP

(57) ABSTRACT

A pant-type disposable wearing article includes at least one waist region of front and rear waist regions, which includes an inner sheet lying on the skin-facing side and an outer sheet lying on the non-skin-facing side. The inner sheet has a contractile force higher than that of the outer sheet at least in the transverse direction X. Opposite lateral sections of the inner sheet and opposite lateral sections of the outer sheet are permanently bonded together and extend outward in the transverse direction X from arrays of side seam spots to form front flaps and rear flaps defining protruding rims. The front flaps and the rear flaps are curled inwardly. This article is improved so that opposite side edges do not irritate a wearer's skin even if the wearer's skin comes in contact with these side edges and, in addition, good appearance from a lateral view is assured.

13 Claims, 6 Drawing Sheets

(56) References Cited

U.S. PATENT DOCUMENTS

| | | | |
|---|---|---|---|
| 5,236,430 A * | 8/1993 | Bridges | 604/396 |
| 5,662,638 A | 9/1997 | Johnson et al. | |
| 6,042,673 A | 3/2000 | Johnson et al. | |
| 6,120,489 A | 9/2000 | Johnson et al. | |
| 6,197,012 B1 | 3/2001 | Mishima et al. | |
| 6,726,792 B1 | 4/2004 | Johnson et al. | |
| 2005/0131374 A1 * | 6/2005 | Otsubo et al. | 604/385.27 |
| 2007/0038199 A1 | 2/2007 | Erdman et al. | |

FOREIGN PATENT DOCUMENTS

| | | |
|---|---|---|
| JP | 10286279 | 10/1998 |
| JP | 11513296 | 11/1999 |
| JP | 2000070300 | 3/2000 |
| JP | 2001527449 | 12/2001 |
| JP | 2002505159 | 2/2002 |
| JP | 4034347 | 1/2008 |
| JP | 2008289611 | 12/2008 |
| WO | 9944559 | 9/1999 |

OTHER PUBLICATIONS

Supplementary European Search Report issued May 27, 2014, corresponds to European patent application No. 10840778.4.

* cited by examiner

PANTS-TYPE DISPOSABLE WEARING ARTICLE

RELATED APPLICATIONS

The present application is a national phase of PCT/JP2010/007573, filed Dec. 27, 2010 and is based on, and claims priority from, Japanese Application Number 2009-298963, filed Dec. 28, 2009.

TECHNICAL FIELD

The present disclosure relates to disposable wearing articles and more particularly to pant-type disposable wearing articles such as pant-type disposable diapers, disposable toilet-training pants, disposable incontinent pants or disposable menstruation pants having opposite side edges sealed.

BACKGROUND

Pant-type disposable wearing articles provided, along respective side edges of their front and rear waist regions, with arrays of side seam spots at which the front and rear waist regions are joined together are known. For example, PATENT DOCUMENT 1 (JP 1986-207605 A) discloses a pant-type disposable wearing article comprising a front waist region, a rear waist region, a crotch region extending between the front and rear waist regions and arrays of side seam spots at which respective side edges of the front and rear waist regions are joined together.

In such articles, the sheet members forming the front and rear waist regions, respectively, extend outward in the transverse direction of the articles from the arrays of the side seam spots to define externally exposed cut edges. Such externally exposed cut edges of the sheet members may create a feeling of discomfort against the wearer if these cut edges come in contact with the wearer's skin. In addition, these cut edges are undesirable from the standpoint of appearance.

Therefore, it is desired to provide an improved pant-type disposable wearing article with opposite side edges that do not irritate the wearer's skin even if the wearer's skin comes into contact with these side edges and, in addition, assures a good appearance from a lateral view.

CITATION LIST

Patent Literature

[Patent Document 1] JP 1986-207605 A

SUMMARY

A pant-type disposable wearing article in accordance with one or more embodiments of the present invention has a longitudinal direction, a transverse direction being orthogonal to said longitudinal direction, a skin-facing side and a non-skin-facing side, and comprises a front waist region, a rear waist region and a crotch region extending between said front and rear waist regions, wherein: at least one of said front and rear waist regions comprises an inner sheet lying on the skin-facing side and an outer sheet lying on the non-skin-facing side wherein the inner sheet has contractile force higher than that of the outer sheet at least in the transverse direction; opposite lateral sections of said inner and outer sheets are permanently bonded together; arrays of side seam spots are provided, which extend in said longitudinal direction and join the front and rear waist regions to one another; and opposite lateral sections of said front and rear waist regions extend outward in said transverse direction from said arrays of side seam spots to form respective pairs of front and rear flaps, which are curled inwardly so as to define protruding rims outside said arrays of side seam spots. Preferably, respective front and rear flaps are curved towards one other.

DETAILED DESCRIPTION

Figure 1:
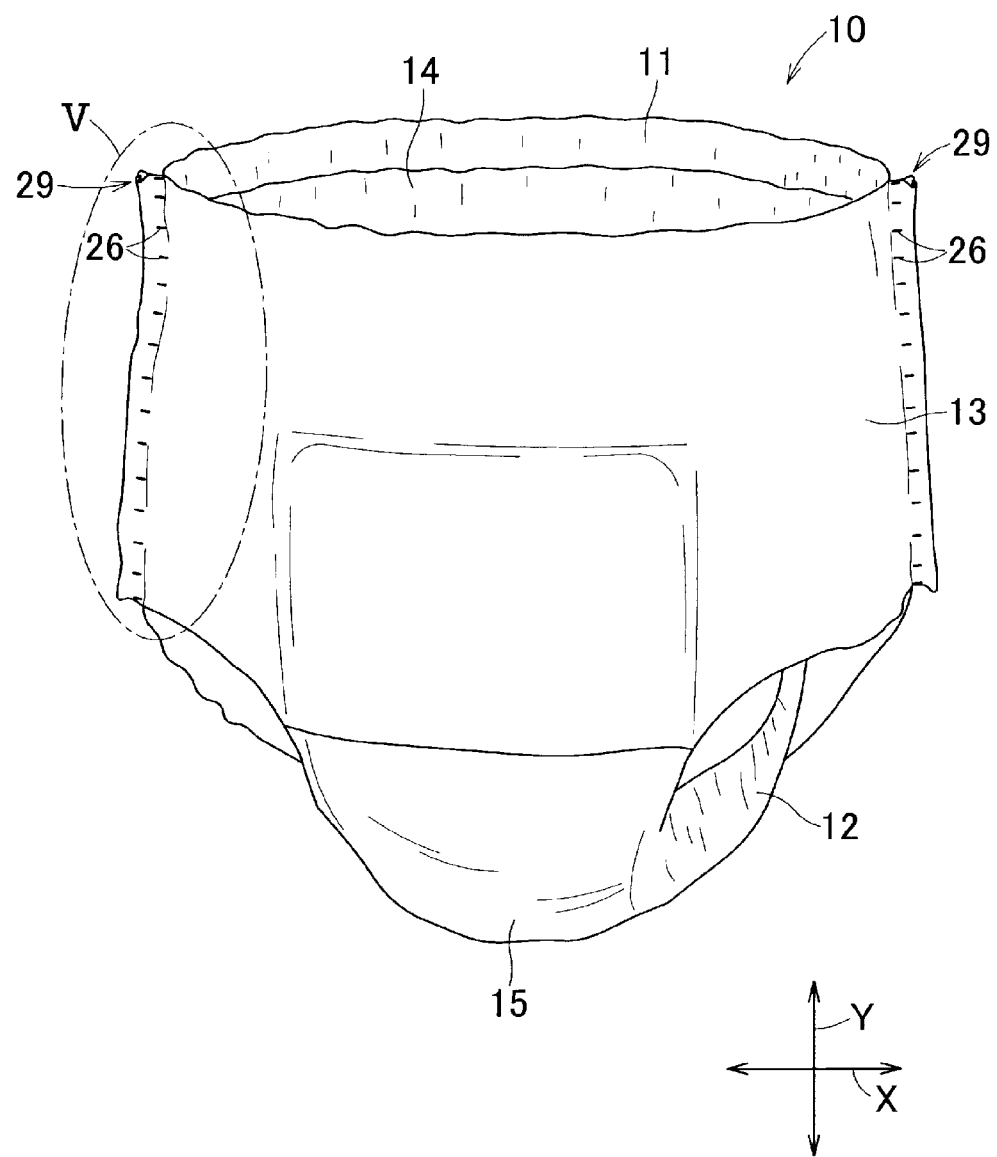
FIG. 1 is a perspective view of a disposable diaper as an example of the pant-type disposable wearing article according to the present invention.
Figure 2:
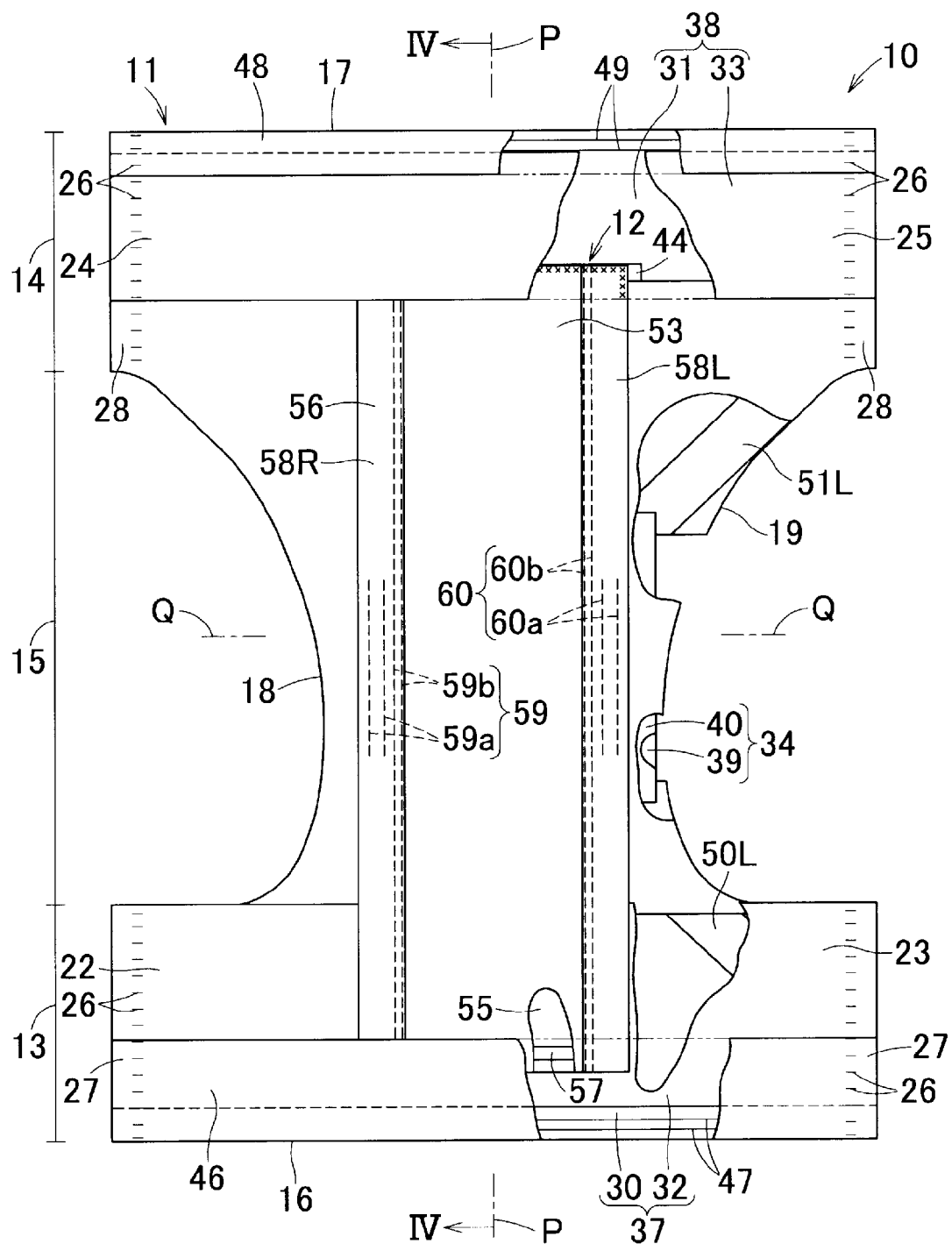
FIG. 2 is a partially cutaway plan view showing the diaper as has been flatly developed.
Figure 3:
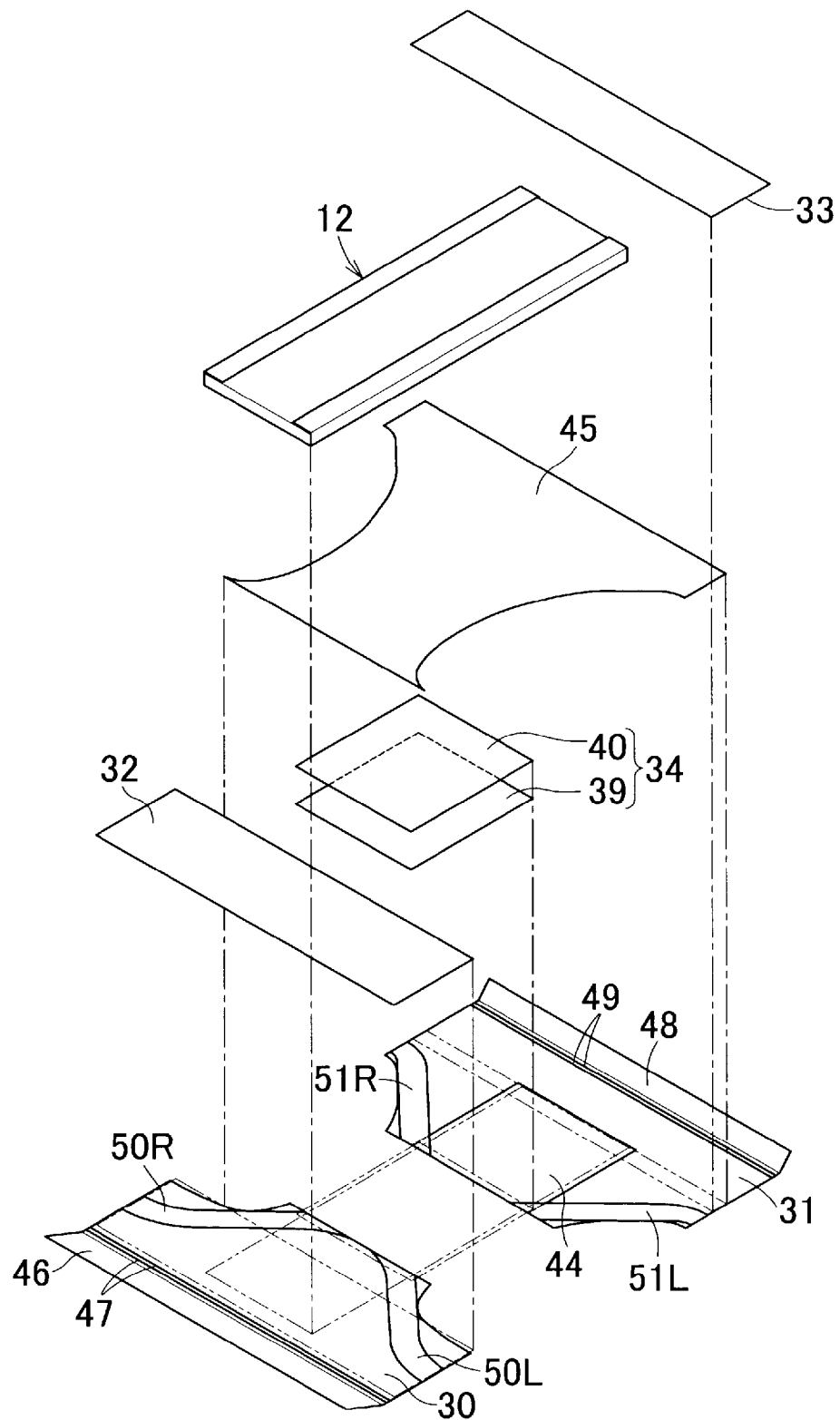
FIG. 3 is an exploded perspective view of the diaper.

As shown in FIGS. 1 and 2, a diaper 10 has a longitudinal direction Y, a transverse direction X which is orthogonal to the longitudinal direction Y, a skin-facing side, a non-skin-facing side, a chassis 11 defining an outer shape of the diaper 10 and a liquid-absorbent structure 12 lying on the skin-facing side of the chassis 11. In FIG. 2, a longitudinal axis of the diaper 10 is designated by P, a transverse axis of the diaper 10 is designated by Q and the diaper 10 is symmetric about the longitudinal axis P.

The diaper 10 comprises a front waist region 13, a rear waist region 14, a crotch region 15 extending between the front and rear waist regions 13, 14, front and rear ends 16, 17 opposed to each other in the longitudinal direction Y and extending in the transverse direction X, and side edges 18, 19 opposed to each other in the transverse direction X and extending in the longitudinal direction Y.

The opposite side edges 18, 19 describe concave curves in the crotch region 15 to fit about the wearer's thighs. Opposite side edges 22, 23 of the front waist region 13 are joined to opposite side edges 24, 25 of the rear waist region 14 at side seam spots 26 arranged intermittently in the longitudinal direction Y to form a waist-opening and a pair of leg-openings. The opposite side edges 22, 23 of the front waist region 13 as well as the opposite side edges 24, 25 of the rear waist region 14 extend outward in the transverse direction X from the side seam spots to define a pair of front flaps 27 and a pair of rear flaps 28. Sheets put flat together are heat sealed together at the side seam spots by heat or supersonic embossing.

The chassis 11 comprises a generally trapezoidal first outer sheet 30 lying on the non-skin-facing side to define the front waist region 13 and a part of the crotch region 15, a generally trapezoidal second outer sheet 31 lying also on the non-skin-facing side to define the rear waist region 14 and a part of the crotch region 15, a first inner sheet 32 extending in the transverse direction X in the front waist region 13 and bonded to the skin-facing surface of the first outer sheet 30, a second inner sheet 33 extending in the transverse direction X in the rear waist region 14 and bonded to the skin-facing surface of the second outer sheet 31 and a generally rectangular middle sheet 34 extending between the first and second outer sheets 30, 31 to define a middle section of the crotch region 15.

Figure 4:
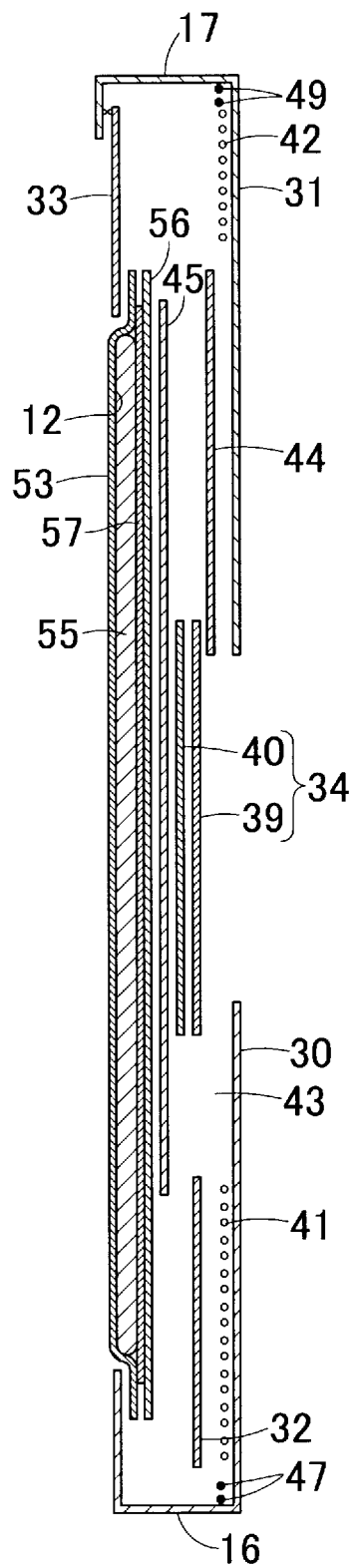
FIG. 4 is a schematic sectional view taken along the line IV-IV in FIG. 2.

Referring to FIG. 4, the first outer sheet 30 and the first inner sheet 32 are bonded to each other by hot melt adhesive 41 to form a first laminated sheet 37. The second inner sheet 33 has a width dimension smaller than the first inner sheet 32 and bonded to the second outer sheet 31 by hot melt adhesive 42 to form a second laminated sheet 38. The middle sheet 34 comprises a generally rectangular fibrous non-woven fabric sheet 39 lying on the non-skin-facing side and a moisture-pervious but liquid-impervious plastic sheet 40 lying on the skin-facing side and generally the same as the fibrous non-woven fabric sheet 39 in shape as well as in size. These two sheets 39, 40 are bonded to each other by hot melt adhesive (not shown) to form the middle sheet 34.

The chassis 11 further includes graphic displaying film 44 printed on its non-skin-facing side with graphics or the like (not shown) adapted to be visually recognizable from the outside and located in a middle section of the rear waist region 14 as viewed in the transverse direction X and a fixing sheet 45 made of fibrous non-woven fabric extending across the crotch region 15 into the front and rear waist regions 13, 14 on the skin-facing side of the chassis 11. The fixing sheet 45 has a width dimension sufficiently larger than that of the middle sheet 34 to cover, in the middle section of the crotch region 15, the entire skin-facing surface of the middle sheet 34.

Along the front end 16 of the front waist region 13, the first outer sheet 30 is folded inward to form a front folded region 46 and two or more first elastic strands 47 made of an elastomeric material are attached under tension and in a contractible manner inside this folded region 46 to be associated with the front waist region 13. Along the rear end 17 of the rear waist region 14, the second outer sheet 31 is folded inward to form a rear folded region 48 and two or more second elastic strands 49 are attached under tension and in a contractible manner inside this folded region 48 to be associated with the rear waist region 14.

Along sections of the side edges of the crotch region 15 in the vicinity of the front waist region 13 which is corresponding to front halves of the leg-openings' peripheral edges, elastic ribbons 50R, 50L made of an elastomeric material are attached under tension and in a contractible manner to the inner surface of the first outer sheet 30 to be associated with the front halves of the leg-openings' peripheral edges. In a similar manner, along sections of the side edges of the crotch region 15 in the vicinity of the rear waist region 14 which is corresponding to rear halves of the leg-openings' peripheral edges, elastic ribbons 51R, 51L made of an elastomeric material are attached under tension and in a contractible manner to the inner surface of the second outer sheet 31 to be associated with the rear halves of the leg-openings' peripheral edges. The fixing sheet 45 is fixed to a partial outer surface of the elastic elements 50R, 50L associated with the front halves of the leg-openings' peripheral edges and to the entire outer surface of the elastic elements 51R, 51L associated with the rear halves of the leg-openings' peripheral edges.

The first and second outer sheets 30, 31 are formed of heat sealable spun bonded fibrous non-woven fabrics having contractile force lower than that of the outer sheet. These outer sheets 30, 31 have a thickness preferably in a range of 0.3 to 0.5 mm, a basis mass preferably in a range of 15 to 40 g/m$^2$, more preferably in a range of 25 to 35 g/m$^2$ and a fiber density preferably in a range of 0.06 to 0.1 g/cm$^3$, more preferably in a range of 0.07 to 0.09 g/cm$^3$. It is possible to form the first and second outer sheets 30, 31 with multiple layers, respectively, and in this case, at least the outermost fibrous layer in each of these multiple layers may be formed of spun bonded filament fibers behaving to crimp.

The first and second inner sheets 32, 33 are formed of air-through fiber (staple) non-woven fabrics or spun bonded non-woven fabrics made of heat sealable and elastically stretchable elastomeric fibers having a thickness preferably in a range of 0.9 to 1.0 mm, a basis mass preferably in a range of 20 to 50 g/m$^2$, more preferably in a range of 30 to 40 g/m$^2$ and a fiber density preferably in a range of 0.01 to 0.04 g/cm$^3$, more preferably in a range of 0.025 to 0.035 g/cm$^3$.

An elongation percentage of the first and second outer sheets 30, 31 is preferably in a range of 100 to 150% and an elongation percentage of the first and second inner sheets 32, 33 is preferably in a range of 150 to 300%. The first and second inner sheets 32, 33 are stretched in the transverse direction X at an elongation ratio in a range of 2.0 to 3.0 and, in this state, bonded to the first and second outer sheets 30, 31 by hot melt adhesive.

While the types of hot melt adhesive 41, 42 used to bond the first and second outer sheets 30, 31 to the first and second inner sheets are not limited to any particular types, rubber-based adhesive, for example, SBS (styrene-butadiene-styrene)-based or SIS (styrene-isoprene-styrene)-based adhesive each having a basis mass in a range of 1.0 to 5.0 g/m$^2$ is preferably used to protect the stretch properties of the first and second inner sheets 32, 33 from being adversely affected by adhesive as reliably as possible. While respective hot melt adhesive 41, 42 may be applied selectively in various well known patterns such as an omega-pattern, a spiral pattern, a dotted pattern, a wavy pattern, two or more adhesive lines extending in the transverse direction X are applied preferably in an omega-pattern. In this case, the adhesive line's diameter is preferably in a range of 0.01 to 0.1 mm, more preferably in a range of 0.03 to 0.07 mm, a distance dimension between each pair of the adjacent adhesive lines is preferably in a range of 1.0 to 2.5 mm, more preferably in a range of 1.5 to 2.0 mm and the area percentage of the adhesive lines with respect to the total inner surface of the first and second inner sheets 32, 33 is preferably in a range of 2 to 10%, more preferably in a range of 4 to 6%.

The middle sheet 34 and the fixing sheet 45 may be formed, for example, of spun bonded fibrous non-woven fabrics or air-through fibrous non-woven fabrics having contractile force lower than that of the first and second inner sheets 32, 33 as in the case of the first and second outer sheets 30, 31.

The liquid-absorbent structure 12 has a rectangular shape contoured by front and rear ends and opposite side edges being orthogonal to the front and rear ends to be relatively long in the longitudinal direction Y. The liquid-absorbent structure 12 extends across the crotch region 15 into the front and rear waist regions 13, 14 and comprises a liquid-pervious top-sheet 53 lying on the skin-facing side, a liquid-absorbent core assembly 55 formed of mixture of fluff pulp fibers and super-absorbent polymer particles covered with a liquid-dispersant sheet (not shown), a cover sheet 56 adapted to wrap the entirety of the liquid-absorbent core assembly 55 and a leak-barrier sheet 57 made of plastic material sandwiched between the liquid-absorbent core assembly 55 and the cover sheet 56.

The cover sheet 56 has lateral sections extending outward in the transverse direction X from opposite side edges of the liquid-absorbent core assembly 55. These lateral sections are partially folded inward to form a pair of sleeve-like side flaps 58R, 58L respectively having therein four elastic strands 59, 60 made of an elastomeric material extending in the longitudinal direction Y and attached thereto under tension and in a contractible manner by hot melt adhesive. Of respective four elastic strands 59, 60, respective two outer elastic strands 59a, 60a are located in a middle section of the crotch region 15 and cooperate with the first and second elastic ribbons 50R, 50L and 51R, 51L associated with the front and rear halves of the leg-openings' peripheral edges to define elastic belts extending along the wearer's inguinal regions. Of respective four elastic strands 59, 60, respective two inner elastic strands 59b, 60b extend across the crotch region 15 into the front and rear waist regions 13, 14 within the respective side flaps 58R, 58L so that the lateral sections of the cover sheet 56 may be spaced from the top-sheet 53 under contraction of the elastic elements 59, 60 to form barrier- or gasket-cuffs adapted to prevent body waste from leaking sideways.

The non-skin-facing surface of the liquid-absorbent structure 12 is entirely or partially fixed to the skin-facing surface of the chassis 11 by hot melt adhesive (not shown). The rear end of the liquid-absorbent structure 12 is sandwiched between the second inner sheet 33 and the second outer sheet 31 and thereby leakage of body waste beyond the rear end of the liquid-absorbent structure 12 can be reliably prevented.

It is possible to arrange the first and second inner sheets 32, 33 to extend from the respective boundaries of the front and rear waist regions 13, 14 into the crotch region 15. Instead of providing the fixing sheet 45 on the skin-facing side, it is possible to form the chassis 11 as a whole only by outer and inner sheets each defining the outer shape of the diaper 10 so that the diaper 10 as a whole may have elastic stretch properties.

Figure 5:
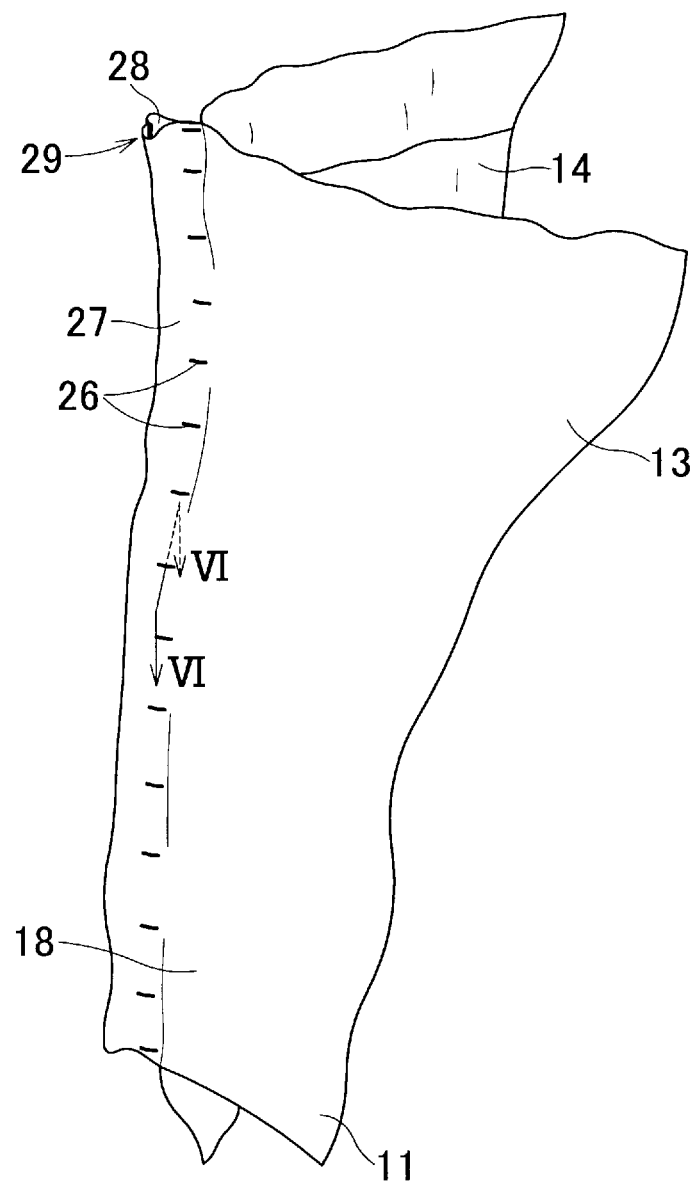
FIG. 5 is a partially scale-enlarged diagram illustrated the region surrounded by dashed-dotted line in FIG. 1.
Figure 6:
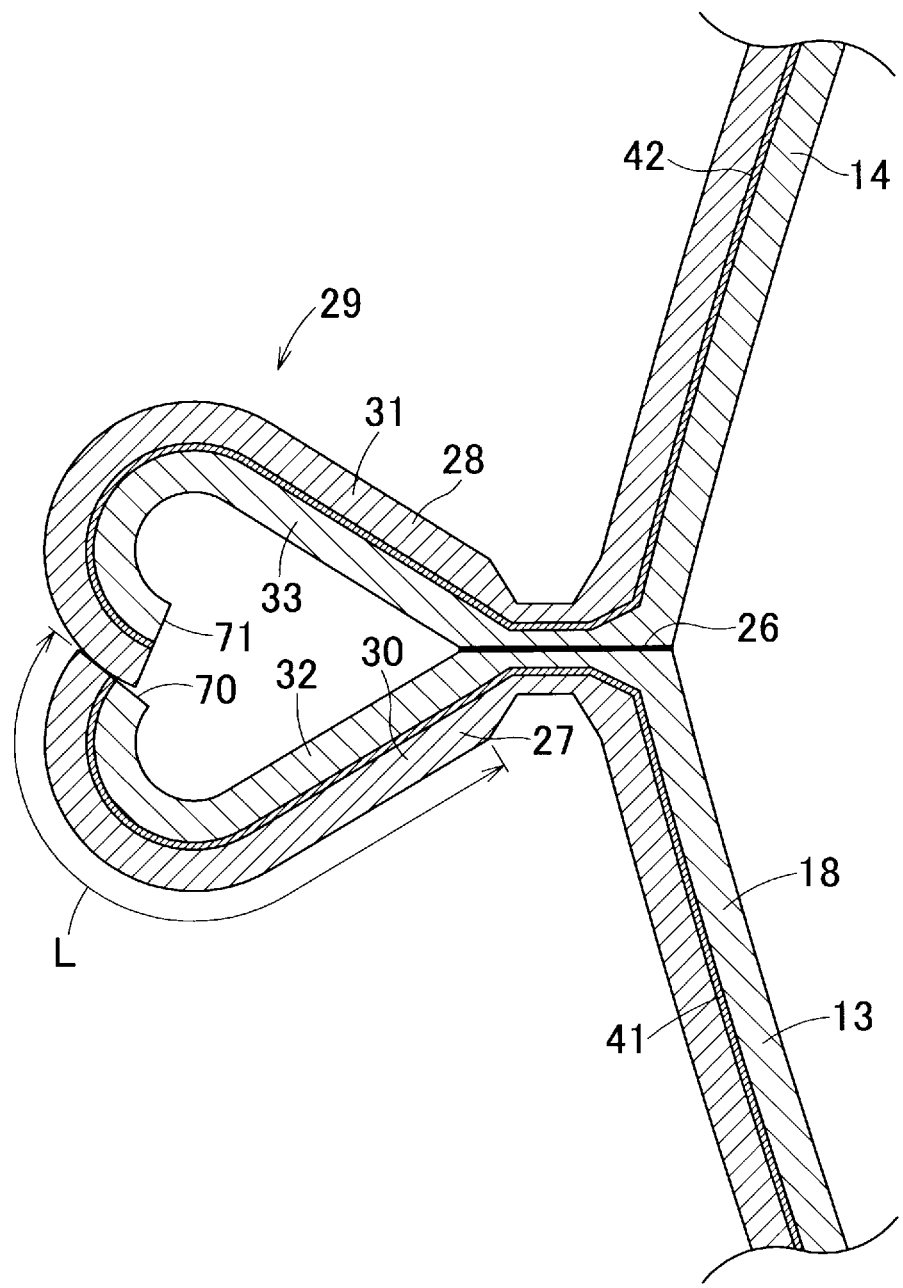
FIG. 6 is a sectional view taken along the line VI-VI in FIG. 5.

As will be apparent from FIGS. 5 and 6, along the opposite side edges 18, 18 of the diaper 10, a pair of the front flaps 27 defined by the side edges of the first laminated sheet 37 and a pair of the rear flaps 28 defined by the side edges of the second laminated sheet 38 extend outward in the transverse direction X from the arrays of side seam spots 26 to form a pair of protruding rims 29. Each of the front flaps 27 is associated with a respective rear flap 28, and the associated flaps 27,28 are curled inwardly towards each other. Outer side edges 70, 71 of the associated front and rear flaps are opposed to each other and may be in contact or with each other or not. A dimension L, which is the width of the front flap 27 in the transverse direction X, is generally the same as that of the rear flap 28 and, specifically, this dimension in the transverse direction X is preferably in a range of about 1.5 to 2.5 mm.

The process of making the diaper 10 includes a step of cutting relevant webs running in a machine direction of the equipment for making the diaper 10 into desired dimensions to obtain the respective sheets 30, 31, 32, 33 and, in this step of cutting, the front flaps 27 and the rear flaps 28 are curled inward so that the cut edges (i.e., the outer side edges 70, 71) are not exposed outward. In consequence, the opposite side edges 18 of the diaper 10 would not irritate the wearer's skin even if the wearer's skin comes in contact with these side edges 18. In addition, compared to the case in which the cut edges of the respective sheets are exposed outward, the diaper 10 looks being soft from a lateral view and thereby assures a good appearance.

The above-described feature of the associated front and rear side flaps 28, 29 curling inwards towards one another to form the protruding rims 29 is brought about by the unique arrangement of the first and second inner sheets 32, 33, which have contractile force, lying on the inner side (i.e., the skin-facing side) and the first and second outer sheets 30, 31, which have contractile force lower than that of the first and second inner sheets 32, 33, being respectively bonded to the first and second inner sheets 32, 33 so as to lie on the outer side thereof (i.e., the non-skin-facing side). Specifically, the first and second inner sheets 32, 33 behave to be curled inward and thereby the first and second outer sheets 30, 31 are forced to be curled inward together with the first and second inner sheets 32, 33. Further preferred features, which may enhance the inward curving, described above, are the application pattern of the hot melt adhesive 41, 42 and the thickness and stiffness of the respective sheets 30, 31, 32, 33. Furthermore, the pressure and/or shape of the cutter may be adapted, in a manner as will be readily appreciated by the skilled person, such that when the regions corresponding to the respective flaps are cut by a cutter as the continuous web comprising a series of the diapers is cut into the individual diapers, the cut edges are curled inwardly. This again enhances the inward curving. If the respective sheets 30, 31, 32, 33 are formed of heat sealable fibers and are cut under heated condition, the outer side edges 70 of the respective front flaps 27 and the outer side edges 71 of the respective rear flaps 28 may be integrally heat sealed together to form continuous annular protruding rims 29.

The first and second inner sheets 32, 33 preferably have stiffness lower than that of the first and second outer sheets 30, 31. Specifically, cantilever measured stiffness value of the first and second outer sheets 30, 31 conducted in accordance with prescription of JIS (Japanese Industrial Standards) L 1096 using CAN-1MC of DAIEI KAGAKU SEIKI MFG.CO, LTD. as a measuring equipment is in a range of 35 to 40 mm in the machine direction (MD) and in a range of 30 to 35 mm in the direction (CD) orthogonal to the machine direction. Cantilever measured stiffness value of the first and second inner sheets 32, 33 conducted in the same manner is in a range of 12 to 17 mm in the machine direction MD and in a range of 15 to 20 mm in the cross direction CD. The particular relationship such that the stiffness of the first and second inner sheets 32, 33 is lower than that of the first and second outer sheets 30, 31 serves to enhance a degree of the deformation occurring in the front and rear flaps and thereby to facilitate these flaps to be curled inward from the inner side. At the same time, the stiffness on the outer side is sufficiently high to restrict a deformation due to external impact force.

The first and second outer sheets 30, 31 may be formed of the sheet members made of crimped fibers or the sheet members containing crimped fibers to enhance a degree of deformation occurring in the first and second outer sheets 30, 31, depending on factors such as a degree of crimping, so that the first and second outer sheets 30, 31 may be noticeably subject to the deforming behavior of the first and second inner sheets 32, 33 and consequently the front and rear flaps 27, 28 may be more reliably curled inward.

As stock materials for the respective components of the diaper 10 according to the present invention, various well known stock materials conventionally used in the relevant technical field may be selectively used unless otherwise specified. Instead of forming the front and rear waist regions 13, 14 by separate sheet members, it is possible to form the front and rear waist regions 13, 14 and the crotch region 15 in an integrated fashion to define the outer shape of the diaper 10.

The aspects of the present invention described above may be arranged in at least following items:

(i) A pant-type disposable wearing article having a longitudinal direction, a transverse direction being orthogonal to said longitudinal direction, a skin-facing side and a non-skin-facing side, comprising a front waist region, a rear waist region and a crotch region extending between said front and rear waist regions, wherein:

at least one of said front and rear waist regions comprises an inner sheet lying on the skin-facing side and an outer sheet lying on the non-skin-facing side wherein the inner sheet has contractile force higher than that of the outer sheet at least in said transverse direction;

opposite lateral sections of said inner and outer sheets are permanently bonded together;

arrays of side seam spots are provided, which extend in said longitudinal direction and join the front and rear waist regions to one another; and opposite lateral sections of said front and rear waist regions extend outward in said transverse direction from said arrays of side seam spots to form respective pairs of front and rear flaps, which are curled inwardly so as to define protruding rims outside said arrays of side seam spots.

Preferably, respective front and rear flaps are curved towards one another.

The aspect of the present invention described in the above item (i) may provide one or more of the following advantageous effects:

(a) In the wearing article according to the present invention, the protruding rims extending outward from the arrays of side seam spots are kept curled inward so that these protruding rims do not irritate the wearer's skin even if the wearer's skin comes in contact with these protruding rims. In addition, the cut edges of the sheet members are not exposed outward so that the wearing article looks being soft from a lateral view and thereby assures a good appearance.

Additionally, one or more of the following embodiments may be provided in accordance with further aspects, which may be taken alone or in combination:

The front and rear waist regions may each comprise an inner sheet lying on the skin-facing side and an outer sheet lying on the non-skin-facing side wherein the inner sheet has contractile force higher than that of the outer sheet at least in the transverse direction, and opposite lateral sections of said inner and outer sheets of each of the front and rear waist regions are permanently bonded together.

The outer sheet may be formed of a sheet member containing crimped fibers.

A thickness of the inner sheet may be in a range of 0.9 to 1.00 mm and a thickness of the outer sheet may be in a range of 0.3 to 0.5 mm.

The basis mass of the outer sheet may be lower than the basis mass of the inner sheet.

The outer sheet may have a basis mass in a range of 15 to 40 g/m$^2$ and the inner sheet may have a basis mass of 20 to 50 g/m$^2$.

The fiber density of the outer sheet may be higher than the fiber density of the inner sheet. The outer sheet may have a fiber density in a range of 0.06 to 0.1 g/m$^3$ and the inner sheet may have a fiber density in a range of 0.01 to 0.04 g/m$^3$.

The elongation percentage of the outer sheet may be lower than the elongation percentage of the inner sheet. An elongation percentage of the outer sheet may be in a range of 100 to 150% and an elongation percentage of the inner sheet may be in the range of 150 to 300%.

The inner sheet may be stretched in the transverse direction and bonded, in this state, to a respective outer sheet. The inner sheet may be stretched at an elongation ratio of 2.0 to 3.0.

The inner sheet may be bonded to a respective outer sheet with an adhesive having a basis mass in a range of 1.0 to 5.0 g/m$^2$. The adhesive may be a rubber-based adhesive. The adhesive may comprise two or more adhesive lines, which extend in the transverse direction. The adhesive lines may extend in an omega-pattern. The adhesive lines may have a width of 0.01 to 0.1 mm, more preferably 0.03 to 0.07 mm. A distance between each pair of adjacent adhesive lines is preferably 1.0 to 2.5 mm, more preferably 1.5 to 2.0 mm. An area percentage of the total inner surface area of the inner sheet that is covered by the adhesive lines is preferably 2 to 10%, more preferably 4 to 6%.

A dimension of the front and rear flaps in the transverse direction may be in a range of 1.5 to 2.5 mm.

The protruding rims may be substantially heart shaped.

The outer side edge of the front flaps may contact the respective rear flaps and the outer side edge of the rear flaps may contact the respective front flaps.

The outer side edge of the front flaps may contact the outer side edge of the respective rear flaps. Outer side edges of the front flaps may be joined to respective outer side edges of the rear flaps so as to form continuous substantially annular protruding rims.

The inner and outer sheets may be formed of heat sealable fibers and the side edges may be joined to one another by heat sealing.

The inner sheet may have a lower stiffness than the respective outer sheet to which it is bonded.

A cantilever measured stiffness value of the outer sheet may be in a range of 35 to 40 mm in the machine direction and in a range of 30 to 35 mm in the direction orthogonal to the machine direction; and a cantilever measured stiffness value of the inner sheet may be in a range of 12 to 17 mm in the machine direction and in a range of 15 to 20 mm in the direction orthogonal to the machine direction.

According to the embodiments detailed in the preceding paragraphs, the advantageous effect(s) set forth at (a) may be better ensured. Further advantageous effects of the respective embodiments may be obtained as discussed in the respective related descriptions.

The invention claimed is:

1. A pants-type disposable wearing article having a longitudinal direction, a transverse direction being orthogonal to said longitudinal direction, a skin-facing side and a non-skin-facing side, said wearing article comprising:
a front waist region, a rear waist region and a crotch region extending between said front and rear waist regions, wherein
at least one of said front and rear waist regions comprises an inner sheet lying on the skin-facing side and an outer sheet lying on the non-skin-facing side, wherein said inner sheet has a contractile force higher than that of said outer sheet at least in said transverse direction,
opposite lateral sections of said inner and outer sheets are permanently bonded together,
arrays of side seam spots extend in said longitudinal direction and join the front and rear waist regions to one another,
opposite lateral sections of said front and rear waist regions extend outward in said transverse direction from said arrays of side seam spots to form respective pairs of front and rear flaps, which are curled inwardly so as to define protruding rims outside said arrays of side seam spots,
the inner sheet has a lower stiffness than the outer sheet bonded to said inner sheet,
a cantilever measured stiffness value of the outer sheet is in a range of 35 to 40 mm in a machine direction and in a range of 30 to 35 mm in a direction orthogonal to the machine direction, and
a cantilever measured stiffness value of the inner sheet is in a range of 12 to 17 mm in the machine direction and in a range of 15 to 20 mm in the direction orthogonal to the machine direction.

2. The wearing article defined by claim 1, wherein
said front and rear waist regions each comprise an inner sheet lying on the skin-facing side and an outer sheet lying on the non-skin-facing side,
said inner sheet has a contractile force higher than said outer sheet at least in said transverse direction, and opposite lateral sections of said inner and outer sheets of each of the front and rear waist regions are permanently bonded together.

3. The wearing article defined by claim 1, wherein the outer sheet includes crimped fibers.

4. The wearing article defined by claim 1, wherein a thickness of the inner sheet is in a range of 0.9 to 1.00 mm and a thickness of the outer sheet is in a range of 0.3 to 0.5 mm.

5. The wearing article defined by claim 1, wherein the outer sheet has a basis mass in a range of 15 to 40 $g/m^2$ and the inner sheet has a basis mass of 20 to 50 $g/m^2$.

6. The wearing article defined by claim 1, wherein the outer sheet has a fiber density in a range of 0.06 to 0.1 $g/m^3$ and the inner sheet has a fiber density in a range of 0.01 to 0.04 $g/m^3$.

7. The wearing article defined by claim 1, wherein an elongation percentage of the outer sheet is in a range of 100 to 150% and an elongation percentage of the inner sheet is in the range of 150 to 300%.

8. The wearing article defined by claim 1, wherein the inner sheet is stretched in the transverse direction and is bonded, in the stretched state, to the outer sheet.

9. The wearing article defined by claim 1, wherein the inner sheet is bonded to the outer sheet with an adhesive having a basis mass in a range of 1.0 to 5.0 $g/m^2$.

10. The wearing article defined by claim 1, wherein a dimension of said front and rear flaps in said transverse direction is in a range of 1.5 to 2.5mm.

11. The wearing article defined by claim 1, wherein the protruding rims are substantially heart shaped.

12. The wearing article defined by claim 1, wherein outer side edges of the front flaps are joined to respective outer side edges of the rear flaps so as to form the protruding rims which are continuous and substantially annular.

13. The wearing article defined by claim 12, wherein the inner and outer sheets are formed of heat sealable fibers and the side edges are joined to one another by heat sealing.

* * * * *